US012758768B2

(12) United States Patent
Nitti et al.

(10) Patent No.: US 12,758,768 B2
(45) Date of Patent: Oct. 13, 2026

(54) IMPLANT TOOL FOR CARDIAC LEADS

(71) Applicant: Cardiac Pacemakers, Inc., St. Paul, MN (US)

(72) Inventors: Benjamin Michael Nitti, Scandia, MN (US); G. Shantanu Reddy, Minneapolis, MN (US); Bryan Peter Nelson, Cushing, WI (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 451 days.

(21) Appl. No.: 18/478,630

(22) Filed: Sep. 29, 2023

(65) Prior Publication Data

US 2025/0108206 A1 Apr. 3, 2025

(51) Int. Cl.
*A61N 1/05* (2006.01)

(52) U.S. Cl.
CPC ...... *A61N 1/057* (2013.01); *A61N 2001/0578* (2013.01); *A61N 2001/058* (2013.01)

(58) Field of Classification Search
CPC ............ A61N 1/057; A61N 2001/0578; A61N 2001/058
See application file for complete search history.

(56) References Cited

U.S. PATENT DOCUMENTS

2020/0222685 A1* 7/2020 De Kock ............... H01R 31/06

* cited by examiner

*Primary Examiner* — Erin McGrath
(74) *Attorney, Agent, or Firm* — Nelson Mullins Riley & Scarborough LLP

(57) ABSTRACT

A tool for implanting a medical lead includes a body having distal region including a distal end, a proximal region including a proximal end, a central axis extending from the distal end to the proximal end, and a midpoint between the distal end and the proximal end. The distal region includes a rounded tip, and a distal lip surrounding a distal opening leading to a distal cavity dimensioned to receive and frictionally engage a connector component of the implantable lead. The proximal region includes a proximal lip surrounding a proximal opening leading to a proximal cavity. A chamber is located between the distal cavity and the proximal cavity. The tool includes a first window. A pair of resilient arms define at least a portion of the chamber and configured to frictionally engage a terminal pin of the implantable lead. The first window, chamber, and pair of resilient arms are located distal of the midpoint.

17 Claims, 9 Drawing Sheets

IMPLANT TOOL FOR CARDIAC LEADS

TECHNICAL FIELD

The present disclosure relates to implant tools for aiding in the implantation of cardiac electrical leads and methods of use. In particular, the present disclosure relates to implant tools fair aiding a user in the implantation of cardiac electrical leads having a fixation element, for example a fixed helical electrode.

BACKGROUND

Cardiac rhythm management systems are useful for electrically stimulating a patient's heart to treat various cardia arrhythmias. These systems include one or more leads configured for implantation adjacent a target heart tissue for stimulating the native conduction system of the heart, e.g., the bundle of His, the left bundle branch and/or the right bundle branch. Such leads may include a fixation element, such as a fixed helical electrode or a freely moving rotatable helical electrode, that can be used to secure the lead to the heart tissue. There is a need for tools to aid in the manipulation and anchoring of these leads during implantation.

SUMMARY

Example 1 is a tool for implanting a medical lead. The tool includes a body having distal region including a distal end, a proximal region including a proximal end, a central axis extending from the distal end to the proximal end, and a midpoint between the distal end and the proximal end. The distal region includes a rounded tip, and a distal lip surrounding a distal opening leading to a distal cavity dimensioned to receive and frictionally engage a connector component of the implantable lead. The proximal region includes a proximal lip surrounding a proximal opening leading to a proximal cavity. A chamber is located between the distal cavity and the proximal cavity. The tool includes first window. A pair of resilient arms define at least a portion of the chamber and are configured to frictionally engage a terminal pin of the implantable lead. The first window, chamber, and pair of resilient arms are located distal of the midpoint.

Example 2 is the tool of Example 1, further comprising one or more indicia located on a surface of the body.

Example 3 is the tool of Example 2, wherein the one or more indicia is raised above the surface of the body or recessed into the surface of the body.

Example 4 is the tool of any of Examples 1-3, further comprising a second window, the second window is located opposite of the first window, and the first window and the second window allow for viewing of the chamber or movement of the pair of resilient arms.

Example 5 is the tool of Example 4, wherein the first window and the second window reduce in cross-section towards the central axis.

Example 6 is the tool of any of Examples 1-5, further comprising a plurality of raised portions, the plurality of raised portions being located on the proximal region.

Example 7 is the tool of Example 6, wherein the plurality of raised portions are equally spaced around the proximal region.

Example 8 is the tool of any of Examples 1-7, wherein the body includes a reduced diameter portion, the reduced diameter portion being located proximal of the midpoint.

Example 9 is the tool of any of Examples 1-8, wherein the distal cavity includes a cylindrical portion and a tapered portion.

Example 10 is the tool of any of Examples 1-9, wherein the chamber includes a substantially square cross-section.

Example 11 is the tool of any of Examples 1-10, wherein the chamber includes an opening and a shoulder, and the chamber tapers from the opening towards the shoulder.

Example 12 is the tool of Example 11, wherein the shoulder is adjacent to a channel extending to the proximal cavity.

Example 13 is the tool of any of Examples 1-12, wherein the proximal lip and the distal lip are rounded.

Example 14 is the tool of any of Examples 1-13, wherein the body is formed as one piece.

Example 15 is the tool of any of Examples 1-14, wherein the proximal opening has a diameter larger than the distal opening.

Example 16 is a tool for implanting a medical lead. The tool includes a body having distal region including a distal end, a proximal region including a proximal end, a central axis extending from the distal end to the proximal end, and a midpoint between the distal end and the proximal end. The distal region includes a rounded tip, and a distal lip surrounding a distal opening leading to a distal cavity dimensioned to receive and frictionally engage a connector component of the implantable lead. The proximal region includes a proximal lip surrounding a proximal opening leading to a proximal cavity. A chamber is located between the distal cavity and the proximal cavity. The tool includes a first window and a second window. A pair of resilient arms define at least a portion of the chamber and configured to frictionally engage a terminal pin of the implantable lead. The first window, the second window, chamber, and pair of resilient arms are located distal of the midpoint.

Example 17 is the tool of Example 16, further comprising one or more indicia located on a surface of the body.

Example 18 is the tool of Example 17, wherein the one or more indicia is raised above the surface of the body or recessed into the surface of the body.

Example 19 is the tool of Example 16, wherein the second window is located opposite of the first window, and the first window and the second window allow for viewing of the chamber or movement of the pair of resilient arms.

Example 20 is the tool of Example 19, wherein the first window and the second window reduce in cross-section towards the central axis.

Example 21 is the tool of Example 16, further comprising a plurality of raised portions, the plurality of raised portions being located on the proximal region.

Example 22 is the tool of Example 21, wherein the plurality of raised portions are equally spaced around the proximal region.

Example 23 is the tool of Example 16, wherein the body includes a reduced diameter portion, the reduced diameter portion being located proximal of the midpoint.

Example 24 is the tool of Example 16, wherein the distal cavity includes a cylindrical portion and a tapered portion.

Example 25 is the tool of Example 16, wherein the chamber includes a substantially square cross-section.

Example 26 is the tool of Example 16, wherein the chamber includes an opening and a shoulder, and the chamber tapers from the opening towards the shoulder.

Example 27 is the tool of Example 26, wherein the shoulder is adjacent to a channel extending to the proximal cavity.

Example 28 is the tool of Example 16, wherein the proximal lip and the distal lip are rounded.

Example 29 is the tool of Example 16, wherein the body is formed as one piece.

Example 30 is the tool of Example 16, wherein the proximal opening has a diameter larger than the distal opening.

Example 31 is a tool for implanting a medical lead. The tool includes a body having distal region including a distal end, a proximal region including a proximal end, a central axis extending from the distal end to the proximal end, and a midpoint between the distal end and the proximal end. The distal region includes a rounded tip, and a distal lip surrounding a distal opening leading to a distal cavity dimensioned to receive and frictionally engage a connector component of the implantable lead. The proximal region includes a proximal lip surrounding a proximal opening leading to a proximal cavity. A chamber is located between the distal cavity and the proximal cavity. The tool includes a first window. A pair of resilient arms define at least a portion of the chamber and configured to frictionally engage a terminal pin of the implantable lead. The first window, chamber, and pair of resilient arms are located distal of the midpoint. The distal opening has a diameter smaller than the proximal opening.

Example 32 is the tool of Example 31, further comprising a second window, the second window is located opposite of the first window, and the first window and the second window allow for viewing of the chamber or movement of the pair of resilient arms.

Example 33 is the tool of Example 32, wherein the first window and the second window reduce in cross-section towards the central axis.

Example 34 is a method of implanting a medical lead. The method includes inserting a proximal end of a lead into a tool having a chamber at least partially formed by a pair of resilient arms. The proximal end of the lead is gripped with the resilient arms. The method includes using a window to verify that the proximal end of the lead is secured in the chamber. The tool is rotated to secure a fixation element of the lead to a desired heart tissue.

Example 35 is a method of Example 34, wherein the fixation element is a helical electrode.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
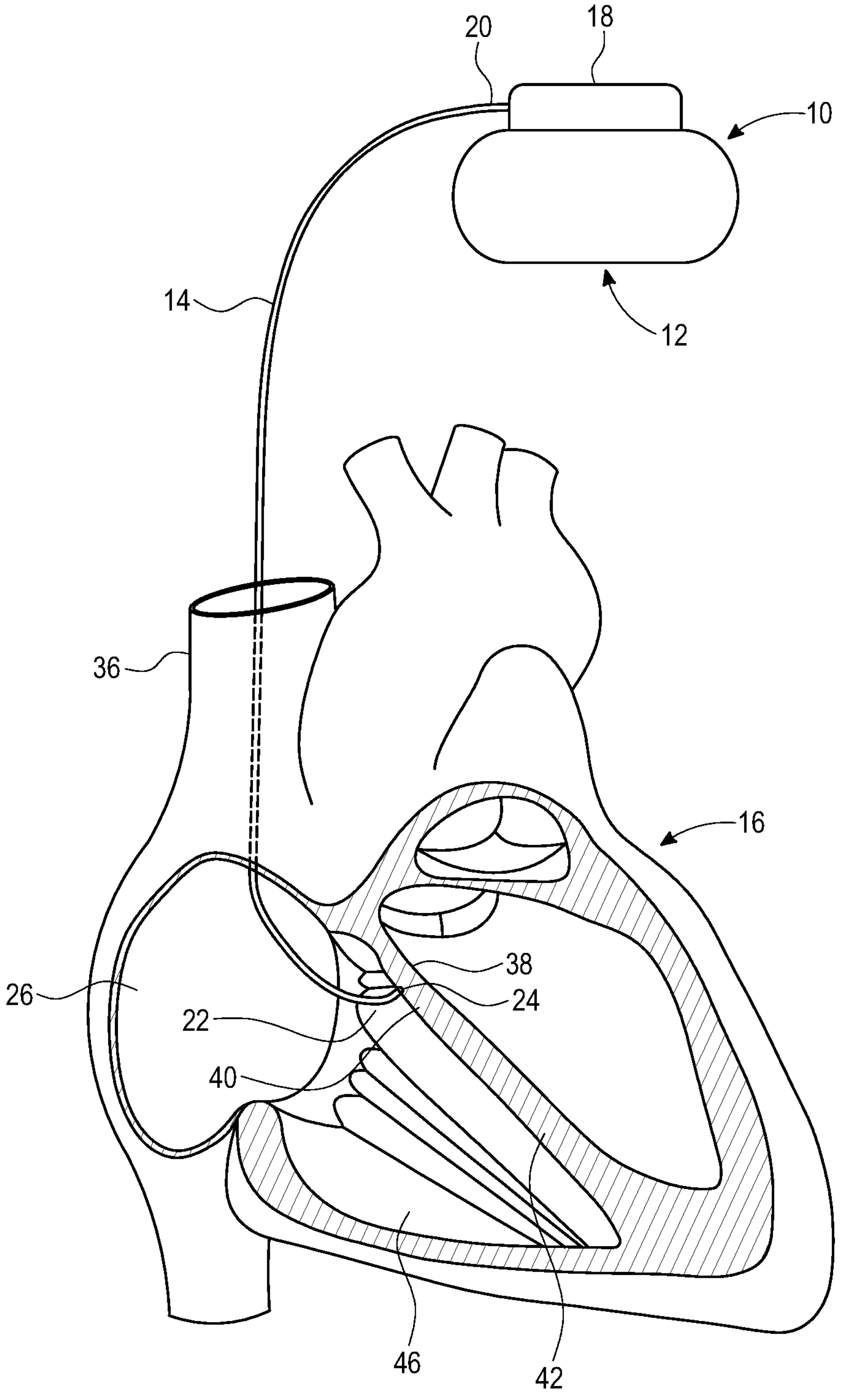
FIG. 1 is a schematic diagram of a conduction system pacing (CSP) system, according to some embodiments of this disclosure.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

The present disclosure concerns, among other things, implanting medical electrical leads having one or more electrodes configured to be secured in contact with, or proximate, the nerve fibers of the native conduction system, in particular the left and/or right bundle branches of the heart.

FIG. 1 is a schematic diagram of a conduction system pacing (CSP) system, according to some embodiments of this disclosure. FIG. 1 illustrates a CSP system 10 including an implantable pulse generator 12 and a lead 14. The lead 14 is implanted in a heart 16. The implantable pulse generator 12 can include circuitry for sensing bioelectrical signals and/or delivering electrical stimulation via the lead 14. The implantable pulse generator 12 can include a lead interface 18 (e.g., a header). The lead 14 can include a proximal end 20, a distal end 22, and a fixation element 24 disposed at the distal end 22.

The lead 14 can further include a proximal connector having one or more electrical contacts (not shown) at the proximal end 20, one or more electrical elements (e.g. ring electrodes) at the distal end 22, and one or more electrical conductors (e.g., one or more coils or one or more cable conductors) (not shown) extending within one or more lumens extending within the lead 14 from the electrical contacts to the electrical elements. The lead interface 18 can connect the pulse generator 12 to the electrical contacts at the proximal end 20 of the lead 14 to electrically connect the pulse generator 12 to the electrical elements.

As shown in FIG. 1, the lead 14 is implanted in a right ventricle 46, at a ventricular septum 42, proximate a left bundle branch 38 and/or right bundle branch 40 of the specialized conduction system. The lead 14 operates to convey electrical signals between the target nerve(s), e.g., the left bundle branch 38 and/or the right bundle branch 40 and the implantable pulse generator 12. In some embodiments, the lead 14 can enter the vascular system through a vascular entry site (not shown) formed in a wall of the left subclavian vein (not shown), extend through the left brachiocephalic vein (not shown) and the superior vena cava 36, to the right ventricle 46. Other suitable vascular access sites may be used in various other embodiments.

The fixation element 24 can fix the lead 14 to cardiac tissue, such as the area of tissue by which the left bundle branch 38 and/or the right bundle branch 40 can be directly stimulated. In some embodiments, the fixation element 24 can be electrically coupled to the implantable pulse generator 12 by, for example, one of the electrical conductors, such as a coil, extending to the proximal end 20 of the lead 14 for interfacing with the lead interface 18. As such, the fixation element 24 can mechanically and electrically couple the lead 14 to the tissue and facilitate the transmission of electrical energy from the conduction system in a sensing mode and to conduction system in a stimulation mode. In some embodiments, the fixation element 24 is a fixed fixation element, such as helix fixed to the lead 14. Such a fixation element 24 can be deployed by rotating the lead 14 itself to implant the fixation element 24 into the tissue. The use of the active fixation element for the fixation element 24 may allow for precise placement of the lead 14. The use of the active fixation element for the fixation element 24 may also provide for mapping capability because the user need not be concerned with accidental entanglement of the helix in the tissue.

While FIG. 1 only shows a single lead connected to the implantable pulse generator 12 and implanted for cardiac stimulation, various other embodiments can have an alternative lead and/or one or more additional leads for sensing bioelectrical activity and/or stimulating other areas of the heart 16.

In some embodiments, as will be discussed in greater detail herein, the CSP system 10 can be capable of both pacing and defibrillation therapies. In such embodiments, the lead 14 can also include one or more high voltage defibrillation electrodes (not shown in FIG. 1) for delivering defibrillation shocks capable of terminating ventricular fibrillation.

Figure 2:
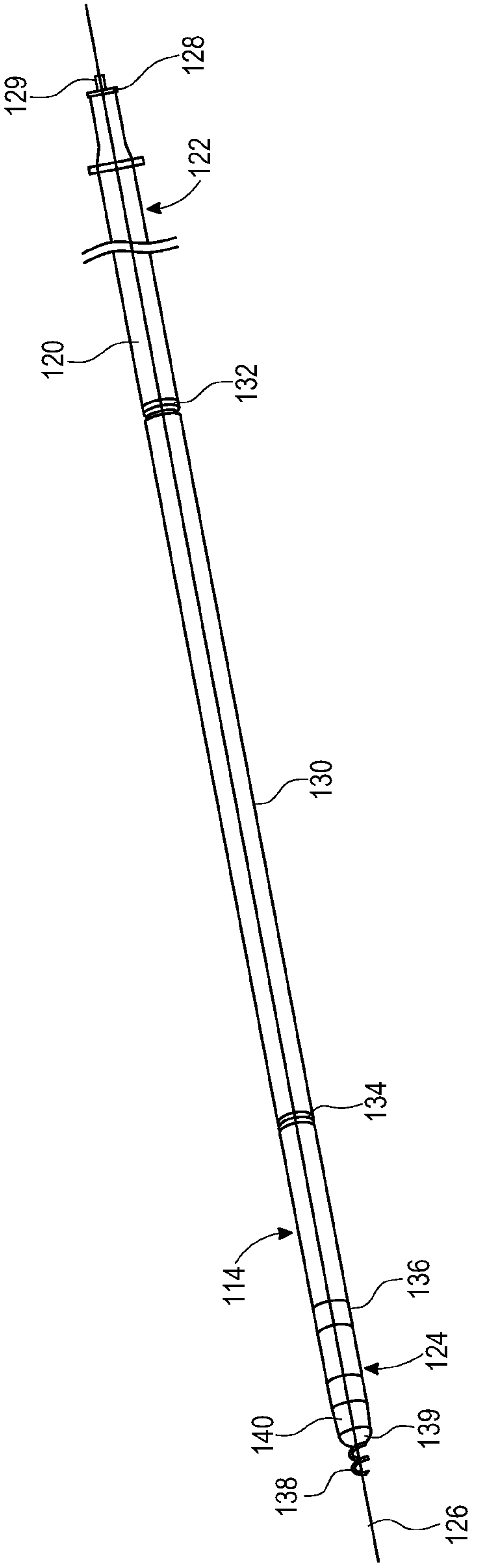
FIG. 2 is a perspective view of a lead, in accordance with embodiments of the subject matter of the disclosure.

FIG. 2 is a perspective view of a lead 114, in accordance with embodiments of the subject matter of the disclosure. The lead 114 includes a flexible elongate body 120 having a proximal region 122 and a distal region 124. The flexible elongate body 120 defines a longitudinal axis 126 of the lead 114. Generally speaking, the proximal region 122 is dimensioned so as to make up the portion of the lead 114 extending from a pulse generator 12 to the location at which the lead 114 enters the right atrium 26 via the superior vena cava 36, whereas the distal region 124 is dimensioned to extend within the heart 16 to the location at which the lead 114 is attached to the interior of the heart 16.

The proximal region 122 includes a connector 128 that is coupled to the proximal end of the flexible elongate body 120. In some embodiments, the connector 128 may include a terminal pin 129 and one or more ring contacts (not shown), to electrically connect one or more active electrodes to the implantable pulse generator 12. In some embodiments, the connector 128 is a conventional bi-polar connector, e.g., an IS-1 connector.

The lead 114 includes a shocking coil 130 positioned along the distal region 124. The shocking coil 130 is positioned between a first shocking coil coupling 132 and a second shocking coil coupling 134.

A ring electrode 136 is also included along the distal region 124. In some embodiments, the ring electrode 136 may be entirely surrounded by insulation rendering the ring electrode 136 inactive. The ring electrode is mechanically and electrically connected to the implantable pulse generator 12 by an electrical conductor that is joined to the ring electrode 136.

The distal region 124 also includes a fixation element in the form of a helical electrode 138 that extends distally from the distal end 139 of the lead 114. The helical electrode 138 is configured to be rotated in order to fix the lead 114 to a desired portion of the interior of the heart 16. In some embodiments, the helical electrode 138 is electrically active and thus can be used to sense the electrical activity of the heart 16 or to apply a stimulating pulse to the cardiac tissue. This would enable a physician to use the helical electrode 138 to map cardiac tissue and thereby identify an optimal attachment site. In other embodiments, the fixation helix is not electrically active and merely operates as a fixation means.

The distal region 124 also includes a drug collar 140. The drug collar 140 includes an exposed surface and is impregnated with a drug or therapeutic. The drug collar 140 is configured to deliver a drug or therapeutic to a desired tissue within the heart 16. In some embodiments, the drug collar 140 is an overmolded collar. In some embodiments, the drug collar 140 is a pre-molded collar.

In order to implant the lead 114 into a desired location in heart or other tissue, the flexible elongate body 120 may be rotated to affix the fixation element to the tissue. In one embodiment, the flexible elongate body 120 may be rotated clockwise to drive the fixation element into the tissue. In another embodiment, the flexible elongate body 120 may be rotated counterclockwise to drive the fixation element into the tissue. FIGS. 2-9 illustrate an implant tool 200 that can be used to grip the proximal end of the lead 114 in order to apply a torque to the flexible elongate body 120. Thus, rotating the fixation element and affixing the lead 114 to a desired tissue location.

Figure 3:
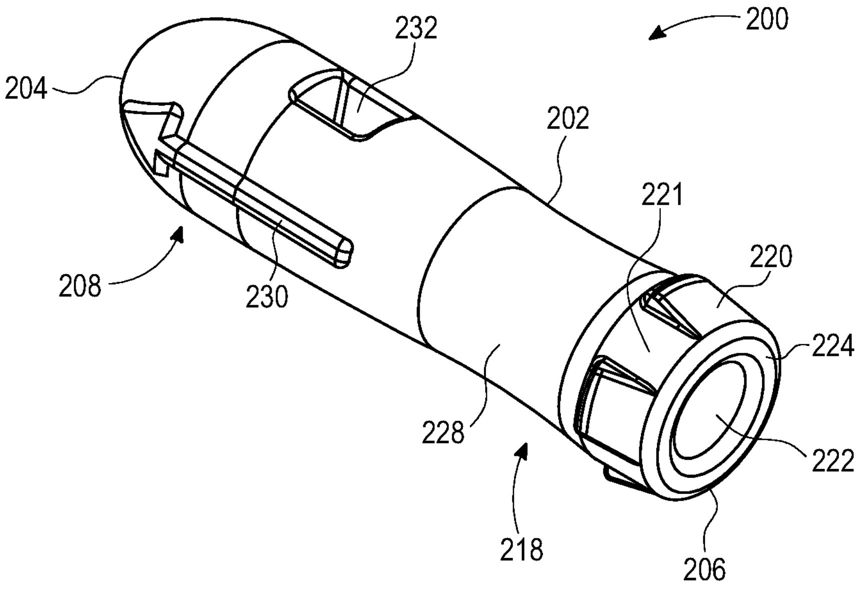
FIG. 3 is a first perspective view of an implant tool for use with a lead, in accordance with embodiments of the subject matter of the disclosure.

FIG. 3 is a first perspective view of an implant tool 200 capable of aiding in the implantation of a lead, in accordance with embodiments of the subject matter of the disclosure. The implant tool 200 includes a body 202 having a generally cylindrical shape extending between a distal end 204 and a proximal end 206. In some embodiments, the body is formed as a single piece of material, for example by a molding process. In other embodiments, the body 202 is made up of several different pieces joined together.

Figure 4:
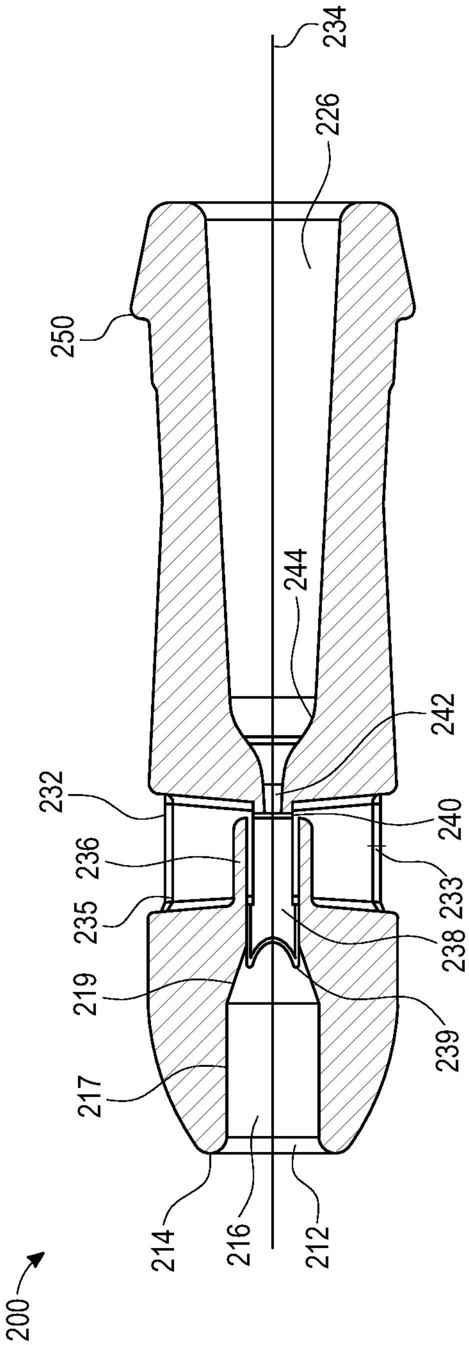
FIG. 4 is a cross-sectional view of the implant tool of FIG. 3, in accordance with embodiments of the subject matter of the disclosure.

A distal region 208 of the body 202 includes a rounded tip 210. The rounded tip decreases in diameter towards the distal end 204. A distal opening 212 is surrounded by a rounded distal lip 214 and is configured for receiving a proximal end of a lead. The proximal end of the lead can include a connector for connecting with a control system, such as an implantable pulse generator 12 (see FIG. 1). As can be seen in FIG. 4, the opening 212 leads to a cavity 216 in the distal region 208 of the implant tool 200. The cavity 216 is sized and shaped to accept and frictionally engage the connector 128 of the lead 114 (see FIG. 2). The cavity 216 includes a cylindrical portion 217 and a tapered portion 219. The tapered portion 219 has a diameter substantially the same as the adjacent cylindrical portion 217, but then reduces in diameter towards the proximal end 206.

A proximal region 218 of the body 202 includes a plurality of raised portions 220. The raised portions 220 are configured to provide surfaces to aid a user in rotating the tool 200. Each raised portion 220 is separated by a gap 221 around the circumference of the body 202 adjacent the proximal end 206. In one embodiment, the raised portions 220 are uniformly spaced around the circumference of the proximal region 218. In another embodiment, the raised portions 220 are spaced at irregular intervals around the circumference of the proximal region 218.

The proximal region 218 includes a proximal opening 222 surrounded by a rounded proximal lip 224. The proximal opening 222 leads to a proximal cavity 226. The proximal opening 222 is configured to receive an elongate medical device, for example a stylet or a guidewire. The elongate medical device can be advanced through the proximal opening 222 into a lumen of a lead held within the tool 200.

The body 202 includes a reduced diameter portion 228 located between the proximal region 218 and the distal region 208. The reduced diameter portion 228 is configured ergonomically to be grasped by a user.

The distal region 208 of the body 202 includes one or more indicia 230. In some embodiments, the one or more indicia 230 is configured to provide visual contrast to a user. The one or more indicia 230 can be printed or otherwise included on a surface of the body 202. For example, the one or more indica 230 can include a printed white arrow. In other embodiments, the indicia 230 can include a portion raised or recessed relative to a surface of the body 202 to provide tactile feedback to a user. The raised or recessed portion can include a color that increases contrast of the one or more indicia 230. The indicia 230 is configured to aid a user in orienting and manipulating a lead during implantation. For example, the indicia 230 can be used by a user to count rotations of the tool 200 in order to ensure sufficient rotation of the fixation element at the desired tissue location. In one embodiment, the one or more indicia 230 is configured as an arrow pointing toward the distal end 204.

Figure 5:
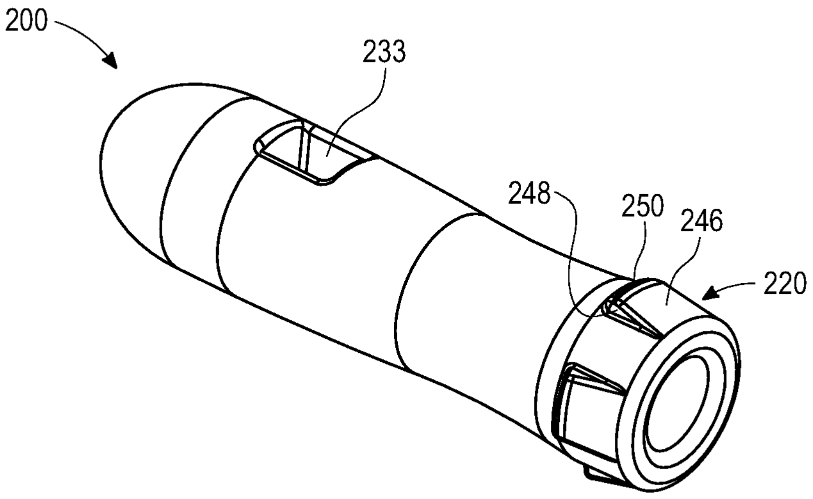
FIG. 5 is a second perspective view of the implant tool of FIG. 3, in accordance with embodiments of the subject matter of the disclosure.

The implant tool 200 includes a first window 232 and a second window 233 (See FIG. 5). The first window 232 and the second window 233 are positioned on opposite sides of the body 202. The first window 232 and the second window 233 allow for visual inspection of a proximal end of lead inserted into the tool 200 as well as provide room for movement of a pair of resilient arms 236. The first window 232 and the second window 233 have a rectangular cross-section.

FIG. 4 is a cross-sectional view of the implant tool 200 illustrated in FIG. 3. As shown, the rectangular cross-section of the first window 232 and the second window 233 reduces in size from an outer surface of the body towards a central axis 234 of the implant tool 200. The walls 235 defining the first window 232 and the second window 233 converge towards the central axis 234. Located adjacent the central axis 234 and viewable from the first window 232 and the second window 233 are a pair of resilient arms 236.

The resilient arms 236 partially define a chamber 238. In one embodiment, the chamber 238 has a substantially rectangular cross-section. The chamber 238 is configured to receive and grip a portion of the proximal region 120 of a lead. The chamber tapers from a distal opening 239 towards a shoulder 240 at the proximal end of the chamber 238. The resilient arms 236 are configured to move away from the central axis 234 while the terminal pin 129 of the lead 114 (see FIG. 2) is inserted into the chamber 238, and to return towards the central axis 234 and apply a force to frictionally engage the terminal pin 129 and secure the connector 128 of the lead 114 (FIG. 2) to the implant tool 200.

In one embodiment, the resilient arms 236 may be connected to the body 202 at a first end, allowing a second end of each arm 236 to move freely. The second end may be biased towards the central axis 234. In this arrangement, the resilient arms 236 may have a substantially linear configuration. In another embodiment, the resilient arms 236 may be connected to the body 202 at a first end and a second end. In this configuration, the arms 236 may have a portion that bows towards the central axis 234. The bowed portion is configured to apply a force to frictionally engage the terminal pin 129 of the lead 114 inserted into the chamber 238.

Referring as well to FIG. 2, the proximal end of terminal pin 129 (is configured to rest against the shoulder 240 when terminal pin 129 is fully inserted into the chamber 238. A channel 242 extends from the shoulder 240 to the proximal cavity 226. The proximal cavity 226 reduces in size from the proximal end 206 to the channel 242. Channel 242 aligns with a lumen of the lead. If a user desires to insert an elongated medical device, such as a stylet or guide wire, into the lumen of the lead, the user can insert the medical device into the proximal opening 222 of the tool 200. During advancement of the elongated medical device, tapered wall 244 will guide the distal end of the medical device towards the channel 242 and into the lumen of the lead, which as the skilled artisan will appreciate, extends through the terminal pin 129 (FIG. 2). In various embodiments, the implant tool 200 has a longitudinal slot (not shown) extending along the length of the body 202 from its outer surface toward the longitudinal axis, which is sized to allow the tool 200 to be loaded laterally over a stylet or similar delivery aid.

FIG. 5 is a second perspective view of the implant tool 200 showing the underside of the tool 200. FIG. 5 shows the second window 233 which is located opposite of the first window 232.

The plurality of raised portions 220 are configured generally as wedges. The plurality of raised portions 220 include a planar surface 246 and two generally triangular side surfaces 248. A distal edge 250 of the raised portions 220 is raised relative to a surface of the body 202. As such, the plurality of raised portions 220 slant downward from the distal edge 250 towards the proximal end 206.

Figure 6:
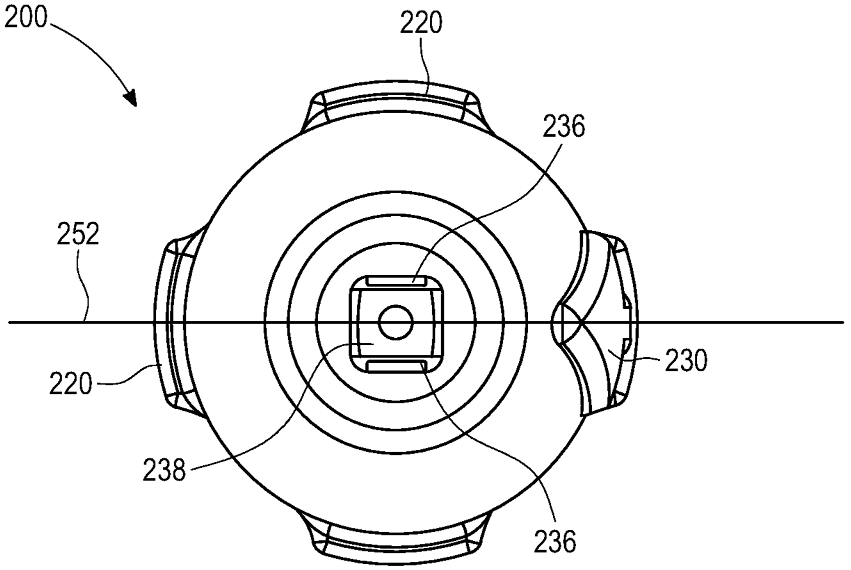
FIG. 6 is a front view of the implant tool of FIG. 3, in accordance with embodiments of the subject matter of the disclosure.

FIG. 6 is a front view of the implant tool 200 of FIG. 3, in accordance with embodiments of the subject matter of the disclosure. In FIG. 6, the chamber 238 formed at least partially by the pair of resilient arms 236 is visible. An axis of symmetry 252 is shown which divides the tool 200 into two identical mirrored halves.

Figure 7:
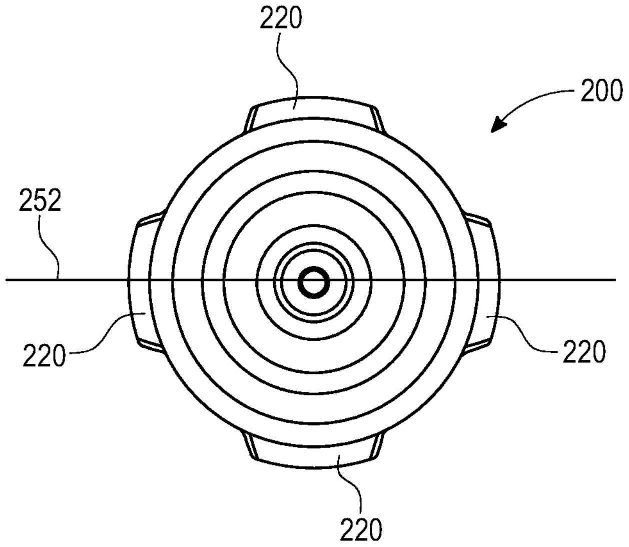
FIG. 7 is a rear view of the implant tool of FIG. 3, in accordance with embodiments of the subject matter of the disclosure.

FIG. 7 is a rear view of the implant tool 200, in accordance with embodiments of the subject matter of the disclosure. In FIG. 7, the plurality of raised portions 220 are shown to be evenly spaced around the proximal region 218. It is understood that while four raised portions 220 are shown, that more or less could be included as desired.

Figure 8:
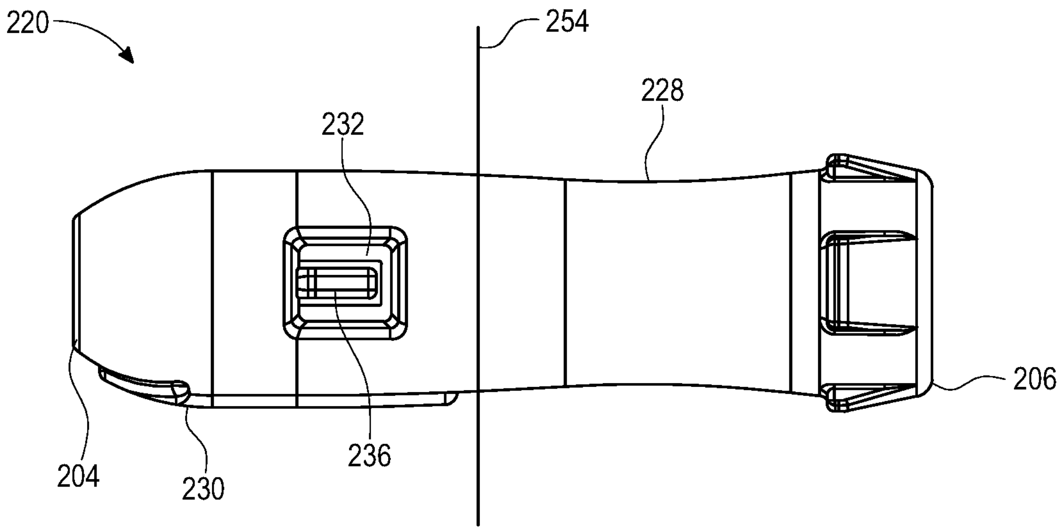
FIG. 8 is a top view of the implant tool of FIG. 3, in accordance with embodiments of the subject matter of the disclosure.
Figure 9:
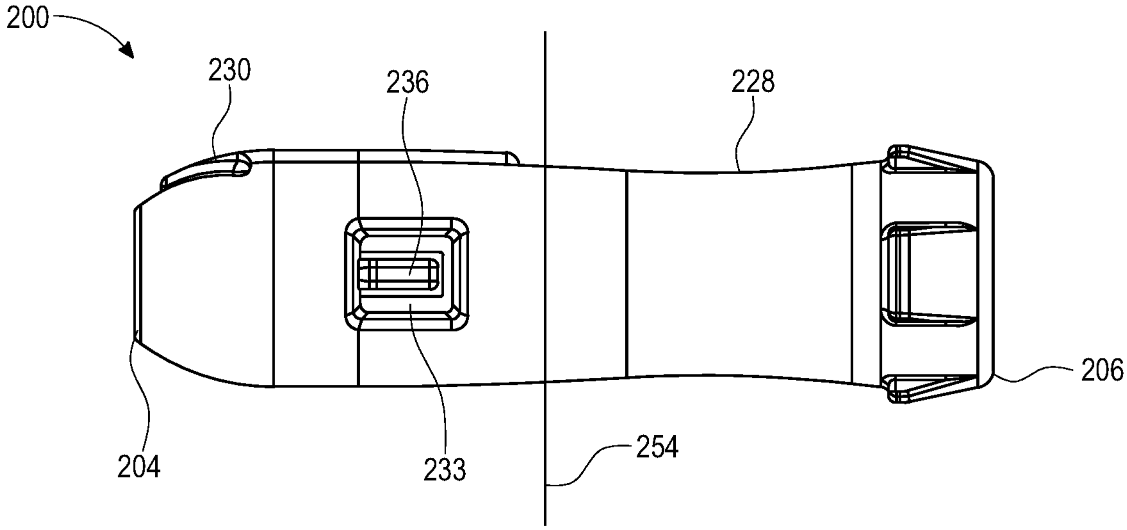
FIG. 9 is bottom view of the implant tool of FIG. 3, in accordance with embodiments of the subject matter of the disclosure.

FIG. 8 is a top view of the implant tool 200 of FIG. 3 and FIG. 9 is a bottom view of the implant tool 200 of FIG. 3, in accordance with embodiments of the subject matter of the disclosure. FIGS. 8 and 9 show a midpoint 254 of the body 202 that lies halfway between distal end 204 and a proximal end 206. The reduced diameter portion 228 is located proximal of the midpoint 254. First window 232, second window 233, resilient arms 236, chamber 238, indicia 230, and rounded tip 210 are each located distal of the midpoint 254. This arrangement ensures comfort to a user during implantation of a lead.

In use, the implant tool 200 facilitates accurate placement and, if necessary, repositioning of the lead electrodes to optimize efficacy of conduction system pacing protocols. Referring to the above figures collectively, during the implantation procedure, the connector 128 of the lead 114 is inserted into the cavity 216 of the implant tool 200, with the terminal pin 129 received within the chamber 238 and frictionally engaged by the resilient arms 236 and the connector 128 frictionally engaged by the walls of the cavity 216. In this way, relative rotation of the lead 114 and the implant tool 200 is inhibited, as well as rotation between the terminal pin 129 and the connector 128. Thus, when the distal end 139 of the lead 114 is positioned at the desired location adjacent target tissue, the user can rotate the implant tool 200 to rotate and screw the helical electrode 138 into the tissue to a desired depth. In embodiments, a stylet inserted into the lead lumen by the aid of the design of the proximal chamber 226 can be used to apply slight distal pressure to facilitate penetration of the helical electrode 138 into the tissue.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A tool for implanting a medical lead, the tool comprising:

a body having a distal region including a distal end, a proximal region including a proximal end, a central axis extending from the distal end to the proximal end, and a midpoint between the distal end and the proximal end;

the distal region including a rounded tip, and a distal lip surrounding a distal opening leading to a distal cavity dimensioned to receive and frictionally engage a connector component of the implantable lead;

the proximal region including a proximal lip surrounding a proximal opening leading to a proximal cavity;

a chamber located between the distal cavity and the proximal cavity, wherein the chamber includes an opening and a shoulder, and the chamber tapers from the opening towards the shoulder;

a first window; and a pair of resilient arms defining at least a portion of the chamber and configured to frictionally engage a terminal pin of the implantable lead;

wherein the first window, chamber, and pair of resilient arms are located distal of the midpoint.

2. The tool of claim 1, further comprising one or more indicia located on a surface of the body.

3. The tool of claim 1, wherein the body includes a reduced diameter portion, the reduced diameter portion being located proximal of the midpoint.

4. The tool of claim 1, wherein the distal cavity includes a cylindrical portion and a tapered portion.

5. The tool of claim 1, wherein the shoulder is adjacent to a channel extending to the proximal cavity.

6. The tool of claim 5, wherein the proximal opening has a diameter larger than the distal opening.

7. The tool of claim 1, wherein the body includes a reduced diameter portion, the reduced diameter portion being located proximal of the midpoint.

8. The tool of claim 7, wherein the chamber includes a square cross-section.

9. The tool of claim 8, wherein the chamber includes an opening and a shoulder, and the chamber tapers from the opening towards the shoulder.

10. The tool of claim 9, wherein the shoulder is adjacent to a channel extending to the proximal cavity.

11. The tool of claim 10, wherein the body is formed of a single piece of material.

12. The tool of claim 10, wherein the proximal opening has a diameter larger than the distal opening.

13. A tool for implanting a medical lead, the tool comprising:

a body having a distal region including a distal end, a proximal region including a proximal end, a central axis extending from the distal end to the proximal end, and a midpoint between the distal end and the proximal end;

the distal region including a rounded tip, and a distal lip surrounding a distal opening leading to a distal cavity dimensioned to receive and frictionally engage a connector component of the implantable lead;

the proximal region including a proximal lip surrounding a proximal opening leading to a proximal cavity;

a chamber located between the distal cavity and the proximal cavity;

a first window and a second window that each reduce in cross-section towards the central axis, wherein the second window is located opposite of the first window, and the first window and the second window allow for viewing of the chamber or movement of the pair of resilient arms; and a pair of resilient arms defining at least a portion of the chamber and configured to frictionally engage a terminal pin of the implantable lead;

wherein the first window, second window, chamber, and pair of resilient arms are located distal of the midpoint.

14. A tool for implanting a medical lead, the tool comprising:

a body having a distal region including a distal end, a proximal region including a proximal end, a central axis extending from the distal end to the proximal end, and a midpoint between the distal end and the proximal end;

the distal region including a rounded tip, and a distal lip surrounding a distal opening leading to a distal cavity dimensioned to receive and frictionally engage a connector component of the implantable lead;

the proximal region including a proximal lip surrounding a proximal opening leading to a proximal cavity;

a chamber located between the distal cavity and the proximal cavity, wherein the chamber includes an opening and a shoulder, and the chamber tapers from the opening towards the shoulder;

a first window; and a pair of resilient arms defining at least a portion of the chamber and configured to frictionally engage a terminal pin of the implantable lead;

wherein the first window, chamber, and pair of resilient arms are located distal of the midpoint, and the distal opening has a diameter smaller than the proximal opening.

15. The tool of claim 14, further comprising a second window, the second window being located opposite of the first window, and wherein the first window and the second window allow for viewing of the chamber or movement of the pair of resilient arms.

16. The tool of claim 15, wherein the first window and the second window reduce in cross-section towards the central axis.

17. The tool of claim 16, wherein the body includes a reduced diameter portion, the reduced diameter portion being located proximal of the midpoint.

* * * * *